(12) United States Patent
Ljungquist

(10) Patent No.: US 6,891,035 B2
(45) Date of Patent: May 10, 2005

(54) PROCESS FOR BULK AUTOCLAVING

(75) Inventor: Olle Ljungquist, Täby (SE)

(73) Assignee: Biovitrum AB, Stockholm (SE)

( * ) Notice: Subject to any disclaimer, the term of this patent is extended or adjusted under 35 U.S.C. 154(b) by 0 days.

(21) Appl. No.: 10/186,548

(22) Filed: Jul. 1, 2002

(65) Prior Publication Data

US 2003/0032622 A1 Feb. 13, 2003

Related U.S. Application Data

(60) Provisional application No. 60/301,480, filed on Jun. 29, 2001.

(30) Foreign Application Priority Data

Jun. 29, 2001 (SE) ................................................ 0102339

(51) Int. Cl.[7] .......................... C07H 1/00; C08B 37/00; C08B 37/10
(52) U.S. Cl. ........................ 536/123.1; 536/21; 536/56; 536/63; 536/84; 536/102; 536/114; 536/122; 536/123.13; 536/124
(58) Field of Search .............................. 536/21, 56, 63, 536/84, 102, 114, 122, 123.1, 123.13, 124

(56) References Cited

U.S. PATENT DOCUMENTS

| | | | |
|---|---|---|---|
| 4,582,900 A | * | 4/1986 | Brandt et al. ................ 536/103 |
| 5,071,977 A | | 12/1991 | Cassels et al. .............. 536/123 |
| 5,079,236 A | * | 1/1992 | Drizen et al. ................. 514/54 |
| 5,580,348 A | * | 12/1996 | Blaney et al. ............... 604/367 |
| 5,621,093 A | | 4/1997 | Swann et al. ............... 536/55.2 |
| 5,981,233 A | | 11/1999 | Ringpfeil .................... 435/71.1 |
| 6,056,950 A | | 5/2000 | Saettone et al. ......... 424/78.04 |

FOREIGN PATENT DOCUMENTS

| | | |
|---|---|---|
| SU | 1682360 A1 * | 10/1991 |
| WO | WO 00/24433 | 5/2000 |
| WO | WO 00/61191 A3 | 10/2000 |

* cited by examiner

*Primary Examiner*—James O. Wilson
*Assistant Examiner*—Everett White
(74) *Attorney, Agent, or Firm*—Fish & Richardson P.C.

(57) ABSTRACT

Process for bulk autoclaving of polysaccharides, wherein the process includes: a) dissolving the polysaccharides in an aqueous solution and mixing until a homogeneous solution is obtained; b) filling the resulting solution in at least one container; c) placing the filled container(s) including the solution in an autoclave; d) placing a sensor in at least one of the containers; and e) autoclaving the filled containers.

20 Claims, 3 Drawing Sheets

-□- autoclaved hyaluronate 18 mg/ml

-△- autoclaved hyaluronate 18 mg/ml

-◇- Healon$^R$ 10 mg/ml

PROCESS FOR BULK AUTOCLAVING

CROSS REFERENCE TO RELATED APPLICATIONS

This application claims priority from Swedish Patent Application No. 0102339-9, filed Jun. 29, 2001, and U.S. Provisional Patent Application Ser. No. 60/301,480, filed Jun. 29, 2001. These applications are incorporated herein by reference in their entirety.

TECHNICAL FIELD

The present invention relates to a process for bulk autoclaving of polysaccharides and especially bulk autoclaving of hyaluronic acid.

BACKGROUND ART

Polysaccharides are used in, for example, medical products. One reason for the addition of the polysaccharides to medical products is to give the medical products a higher viscosity. This is needed in for example tissue treatment compositions, such as adhesive compositions in order to make them easier to handle. The polysaccharides may in some cases be mixed with some proteins and they usually need to be sterilized when used in a medical product.

Proteins are sensitive to heat and cannot be heat sterilized, and they are usually filter-sterilized. However, polysaccharides are not possible to filter-sterilize due to the high viscosity and the high molecular weight of these substances. Hence, there is a need to sterilize polysaccharides in order to be able to use them in medical products. However, polysaccharides are also heat sensitive and they are degraded by heat and especially if they have to spend a long time under heat treatment. If they are degraded, they will loose viscosity and would not be as useful any longer or could not be used at all.

Heat sensitive products have been sterilized in some different ways. WO 00/24433 describes a method of reducing degradation of heat sensitive components, such as glucose, in medical substances during heat sterilization. This is made by using a multiple chamber recipient that comprises a first chamber with a first medical substance and at least one second chamber containing an amount of a second medical substance that is smaller than that of the first medical substance. The first chamber is heated to a predetermined temperature for sterilizing the medical substances, and the second chamber is thermally insulated during heating of the multiple chamber recipient. The thermal insulation of the second chamber is removed so that a defined hold time of the second chamber at the sterilization temperature is obtained. The content of the different chambers may then be mixed together.

The process according to the invention especially relates to autoclaving of hyaluronic acid. U.S. Pat. No. 5,621,093 describes a way of steam-sterilizing solid hyaluronic acid in order to overcome disadvantages with chemical sterilization, dry heating and sterilizing hyaluronic acid in solution. These may cause chemical contamination and reduction in molecular weight.

Healon® is the brand name of a product comprising hyaluronic acid, manufactured by Pharmacia AB, and Healon® is sterilized in small glass vessels with a volume of about 1 ml. Hence, these vessels are very small. There is now a need of bulk autoclaving polysaccharides, and especially hyaluronic acid. The purpose with the invention is to solve the problems mentioned above, and reduce the viscosity decrease in bulk autoclaving, which has not been possible before.

SUMMARY OF THE INVENTION

The present invention relates to a process for bulk autoclaving of polysaccharides, comprising dissolving the polysaccharides in a solution, filling the resulting solution in containers in an amount such that the thickness of the container including the solution is less than 15 mm, and autoclaving the filled containers, comprising heating the solution to a predetermined temperature, and starting cooling when $F_0 > 8$. The solution will remain above the predetermined temperature for a predetermined time.

It has been found that the viscosity of the polysaccharides, autoclaved in the process according to the invention, is reduced in some extent, but to an acceptable level. The reduction in viscosity is small, and the viscosity is still satisfactory. Therefore the sterilized solutions will be able to use for its purpose, since the process is gentle to the molecular weight.

DETAILED DESCRIPTION OF THE INVENTION

The invention relates to a process for bulk autoclaving of polysaccharides, wherein the process comprises the steps of dissolving the polysaccharides in an aqueous solution at a pH of about 6 to 8 and mixing until a homogeneous solution is obtained, filling the resulting solution in at least one container in an amount such that the thickness of the container including the solution is less than 15 mm, placing the filled container(s) including the solution in an autoclave, placing a sensor in at least one of the containers, and autoclaving the filled containers, comprising heating the solution to a predetermined temperature, where after cooling is started when $F_0 > 8$, and the solution remains above the predetermined temperature for a predetermined time.

Figure 4:
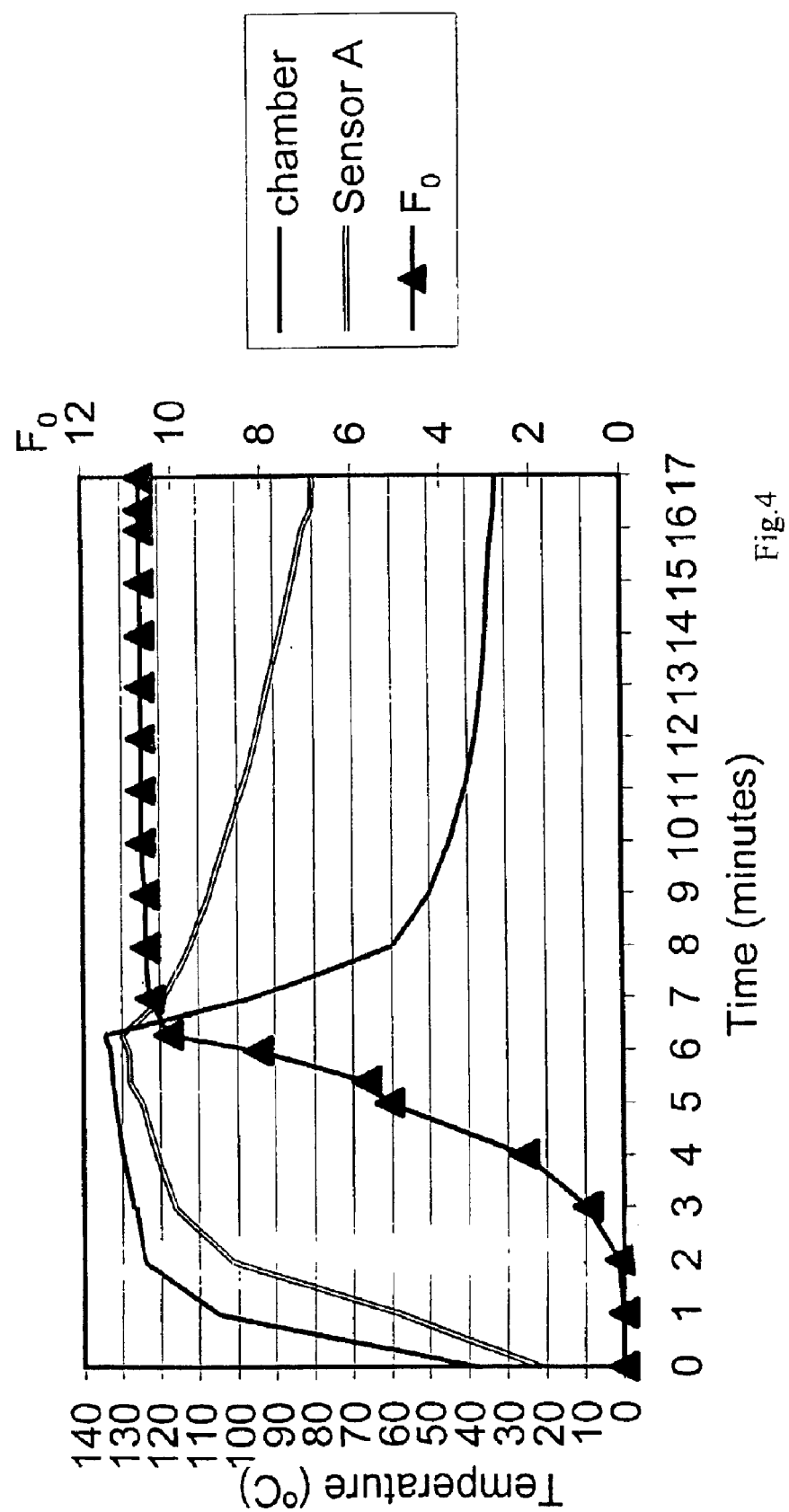
FIG. 4 is a graph depicting curves for the temperature of the autoclave chamber, the temperature of the sensor placed in the container and the $F_0$ value plotted against the time from Example 1.

Any kind of autoclave may be used as long as the solution is heated to the predetermined temperature, where cooling is started when $F_0 > 8$. The cooling which starts is the cooling of the autoclave and at the same time the solution is cooled. However, the solution will be cooled slower than the autoclave, which can be seen in FIG. 4 showing temperature from a process according to the invention. The $F_0$ value reaches maximally about 10 to 12 during the process, and the process is completed in an advantageously short time, thereby reducing degradation of polysaccharides.

F is utilized as a gauge of the capacity of a sterilization process to kill microbes, or the sterilization capacity of a sterilization process. It is a reference gauge and signifies a specific rate of microbes killed during a sterilization process, F representing the time required to achieve this specific death rate at 121° C.

The concept of $F_0$ started being used in pharmaceutical sterilization when it was introduced by the FDA in the "Proposed Rules for LVP" in 1976. The lethal effect of the sterilization is calculated by relating it to a hypothetical sterilization performed at the constant temperature of 121.11° C. for a time $t_{121.11°}$ (121.11° C. is the temperature which corresponds exactly to 250° F.; for the sake of simplicity, we shall continue to deal with $F_0$ as if it corresponds to the temperature 121.0°). The time thus calculated is $F_0$. This calculation can naturally be performed, with a few additional complications, even if the sterilization temperature does not remain constant at T but oscillates around that value during the time t. In mathematical terms, $F_0$ is expressed as follows:

$$F_0 = \Delta t \sum 10^{\frac{T-121}{Z}}$$

where delta t=time interval between measurement of T
T=temperature of the sterilized product at time t
Z=temperature coefficient, assumed to be equal to 10.

Figure 1:
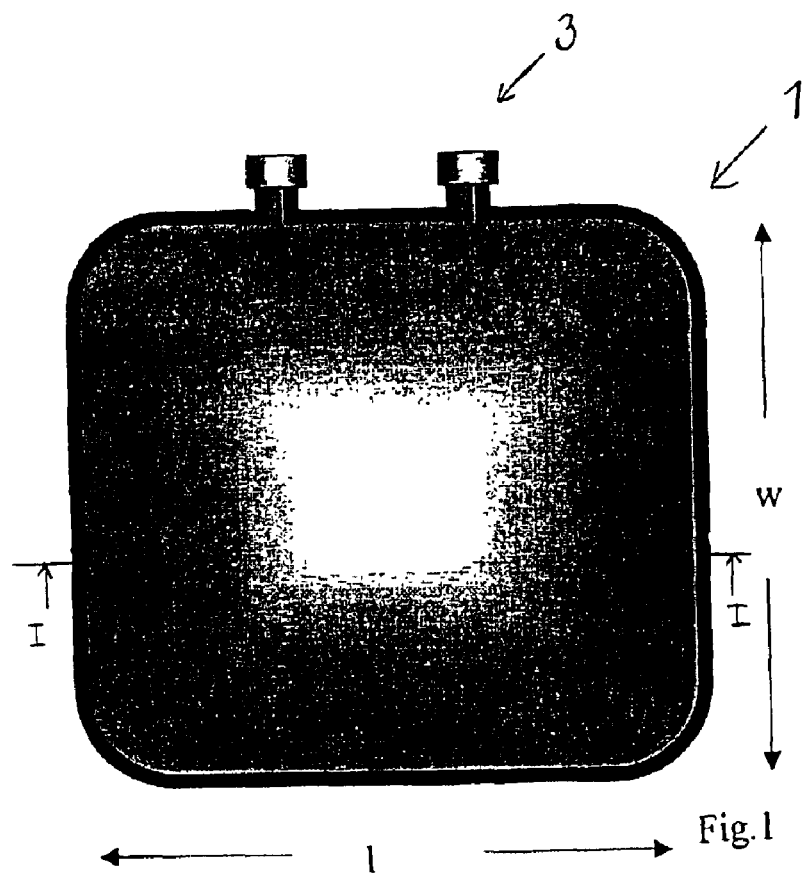
FIG. 1 depicts a top view of a container, which is a plastic bag.
Figure 2:
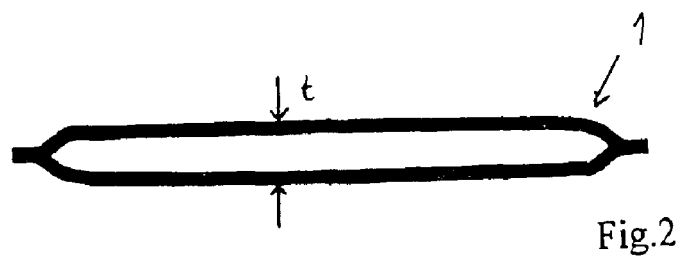
FIG. 2 depicts a cross section at line I—I in FIG. 1 of a plastic bag containing solution according to the invention.
Figure 3:
FIG. 3 depicts a cross section at line I—I in FIG. 1 of a conventional plastic bag containing solution.

A container 1 is shown in FIG. 1, which is a top view of a plastic bag 1, which is a preferred type of container according to the invention. The container has ports 3 shown in the Figure. A cross section of the solution containing plastic bag 1, according to the invention, at line I—I in FIG. 1 is shown in FIG. 2. As a comparison a cross section of a conventional solution containing plastic bag 2 is shown in FIG. 3.

The thickness t, shown in FIG. 2, of the container including the solution is preferably less than 10 mm and mostly preferred less than 7 mm. The container is preferably a plastic bag 1 and a suitable material for the plastic bag is polytetrafluoroethylene or another polymer material that can withstand high temperatures.

The container 1, which in the preferred embodiment is a plastic bag 1, has three extensions in the space. The plastic bag 1 has essentially a width, w, a length, l, and a thickness, t. In this context, the thickness, t, has the smallest value. Hence, if a plastic bag 1 is lying flat on a support (seen from above in FIG. 1), the thickness, t, is the extension perpendicular against the support. The thickness, t, is shown in FIG. 2. The width, w, and the length, l, have larger values than the thickness, t. However, the most important is that the thickness, t, has a smaller value than 15 mm. The bag 1 is flexible, and the thickness, t, gets higher when the solution is filled into it and the thickness, t, of the bag 1 will be maximally 15 mm. A plastic bag 1 is a preferred container 1, but other containers are also possible. They may also have essentially a width, w, a length, l, and a thickness, t, where the thickness, t, has the smallest value. Other forms of the container are of course possible, such as irregular forms. But there is a thickness, t, of the container, which has the smallest value of the extensions in the space of the container 1, and this thickness, t, is less than 15 mm. The container may be flexible or rigid.

The amounts of the polysaccharides to be autoclaved can be about 250 ml or larger. This has not been possible before. If these amounts are put in a bottle, the time to reach a temperature in the middle of the bottle, which is high enough for sterilization would be too long. Such a long time would degrade the polysaccharides. Plastic bags that are used for autoclaving may have a volume of about one or two liters. If such bags would be used with those volumes, the required time for autoclaving would also be too long and the polysaccharides would be degraded. According to the invention, it has been found that when filling the plastic bags 1 to a smaller degree, e.g., until the thickness, t, of the bag 1 including the solution is less than 15 mm, the time for autoclaving the polysaccharides is not so long. The degradation of the polysaccharides is acceptable. The shorter time for autoclaving is due to the heat transforming is easier in a thin plastic bag than in a filled plastic bag or in a bottle containing the same amount.

The volume 250 ml charged in the bags of one or two liters have been used, since these bags are commercially available. Other volumes are also possible, as long as the thickness of the containers is, for example, less than 15 mm, preferably 10 mm and mostly preferred 7 mm.

The polysaccharides are water-soluble, which is a necessary property of the component used. Other water-soluble polymers may also be used. They should have a viscosity-increasing effect in solution, which is an important property for its use in medical substance. The viscosity is dependent on concentration and molecular weight of the polymer.

The polysaccharides may be, for example, glucose aminoglycans and they are selected among heparin sulfate, chondroitin sulfate or their salts or derivatives thereof.

The polysaccharides may also be selected among hyaluronic acid, carboxymethyl cellulose, xanthan, gum arabic, starch or their salts or derivatives thereof According to the invention, the salts or derivatives of the polysaccharides may always be used and is also referred to even if not explicitly mentioned.

The polysaccharide is preferably hyaluronic acid or salts or derivatives thereof and a suitable hyaluronic acid is sodium hyaluronate. Hyaluronic acid is viscosity increasing in a solution and it does also have therapeutic and pharmaceutically good effects when used in medical substances.

The hyaluronic acid or the polysaccharides autoclaved according to the process is suitable for use in medical substances. For simplifying we mention hyaluronic acid in the following, but any suitable polysaccharide could also be used. In order to produce medical substances, the hyaluronic acid may be mixed with proteins. These are heat sensitive and can not be autoclaved. The proteins are usually filter sterilized and may then be mixed with the hyaluronic acid.

An example of a protein is thrombin, which may be mixed with the hyaluronic acid. This mixture may be used together with another component to form a medical substance, which may be an adhesive substance, wound healing substance, hemostatis substance etc. These medical substances are usually mixed with fibrin or fibrinogen. Other conventionally used components may also be included in the medical substances. U.S. Pat. No. 5,631,011 discloses medical substances, such as tissue treatment compositions, comprising fibrin or fibrinogen and viscosity increasing polymers, for example hyaluronic acid. Thrombin may also be used in the compositions. The compositions are two component compositions. The components may be mixed directly when the composition shall be used, for example at a surgery operation. Nothing is said in this document about the sterilization of the hyaluronic acid. However, the amounts used when applying the medical substances are usually small and there is no need for bulk autoclaving in the amounts which are necessary according to the invention.

An advantage with using hyaluronic acid in the compositions above, described in U.S. Pat. No. 5,631,011, is that the hyaluronic acid improves the viscosity properties in the tissue treatment compositions. For example, adhesive components with a water-like fluidity leads to difficulties when handling the glue. In solution, the hyaluronic acid adopts a conformation of very extended random coils, that already at low concentrations entangle into a flexible molecular network that gives the hyaluronate interesting rheological properties. Besides, hyaluronic acid also has a therapeutic and pharmaceutical effect. When hyaluronic acid is used in a treatment composition, the viscosity is improved and adapted to a good level. There is now a need for larger volumes of sterilized hyaluronic acid and that problem is solved according to the invention. When hyaluronic acid is used in U.S. Pat. No. 5,631,011, Healon® is used, which was the only commercial available hyaluronic acid. The containers for Healon® are very small, about 1 ml. There is now an interest for mixing hyaluronic acid with a suitable protein, such as thrombin, and larger amounts can be produced when autoclaving the hyaluronic acid and then mixing with the thrombin. The mixed thrombin and hyaluronic acid is then in a further step distributed in smaller containers in a suitable size.

The hyaluronic acid is preferably mixed with a protein. An especially preferred protein is thrombin. Thrombin is sensitive to alkali and acidic environment, and the pH is therefore about 6 to 8 of the buffer for autoclaving which is adapted to the thrombin. A low content of a helping salt is also necessary and calcium chloride may be used for this purpose. The buffer to solve the hyaluronic acid before the autoclaving is thus adapted to the thrombin. This environment is not optimal for the hyaluronic acid and it leads to a small degradation of the hyaluronic acid. However, the degradation is acceptable for the use of the hyaluronic acid. The autoclaving does also degrade the hyaluronic acid and this degradation is also acceptable. The autoclaving according to the invention is the first that is at all possible in these amounts.

The hyaluronic acid is preferably dissolved in a buffer comprising
  0.045 to 0.055 M Arg, HCl
  0.045 to 0.055 M Gly
  0.045 to 0.055 M Lys, HCl
  0.01 to 0.18 M NaCl
  0.035 to 0.045 M $CaCl_2 2H_2O$
and the hyaluronate is dissolved in an amount of at most 23 mg/ml.

The hyaluronate is preferably dissolved in an amount of 10–23 mg/ml. More than 23 mg/ml is not possible to dissolve and the viscosity would not be high enough if the concentration would be lower than 10 mg/ml. However, in some applications, the viscosity does not need to be high and the hyaluronate could be dissolved in an amount of about 0.1–10 mg/ml. In another application, the concentration of hyaluronate could be 5–15 mg/ml.

The hyaluronate is dissolved in the buffer and mixed until a homogenous solution is obtained. This may take about two days. The solution is filled into plastic bags 1, which are put in an autoclave and a sensor is put in at least one of the bags. The bags used in the Examples below had a width, w, of 170 mm, a length, l, of 170 mm, and a thickness, t, of 7 mm. Other lengths, l and widths, w are possible but the thickness is always below 15 mm. The autoclaving is performed by first heating the solution to a predetermined temperature. This temperature is about 121 to 130° C. and the solution is heated to this temperature within about 3 to 7 minutes. Any type of autoclave may be used, which has an autoclave program which is able to calculate the $F_0$ value and the cooling starts when $F_0 > 8$. The cooling refers to the autoclave cooling. In FIG. 4, it can be seen that the cooling of the autoclave is started when $F_0$ is about 8. It can also be seen that the solution also starts to be cooled at the same time. When the solution has been heated, it will remain at the predetermined temperature for a predetermined time, about 3 to 6 minutes. To avoid inflation of the bags, counter-pressure may be used. The counter-pressure may be performed by means of nitrogen gas. The heating and cooling cycle should be as short as possible, to avoid degradation. The $F_0$ value reaches maximally about 10 to 12 during the autoclaving process. The solution is cooled for about 5 to 12 minutes to a temperature of about 65 to 90° C. It can be seen in FIG. 4 that this cooling starts about the same time as the cooling of the autoclave. The whole process is completed after about 11 to 25 minutes, which is an advantageously short time. An even more preferred interval is 11 to 20 minutes. The time limit is when no killing is obtained any longer and this should be verified microbiologically.

When using such thin bags 1, as according to the invention, the energy transfer is rapid and temperature gradients are avoided. This leads to the possibility of bulk autoclaving of these sensitive materials, which have not been possible in these amounts before.

The buffer in which the hyaluronic acid is dissolved is adapted for being mixed with thrombin as mentioned above. This buffer is not optimal for the hyaluronic acid and there is some degradation of the hyaluronic acid. However, the degradation on account of the buffer and on account of the autoclaving is acceptable. The viscosity is still high enough to use in for example medical substances.

The hyaluronic acid may also be autoclaved in another buffer according to the process described inhere. Such a buffer may be a weak phosphate buffer. But any suitable buffer may be used.

An advantage with the process is that the whole process is over in about 11 to 25 minutes, preferably in 11 to 20 minutes, and the sterilization cycle is terminated when $F_0>8$, i.e. the cooling starts when $F_0>8$. Besides, first of all, it has not been possible at all to sterilize hyaluronic acid in amounts of about 250 ml.

If the autoclaved hyaluronate is used together with thrombin, the thrombin and hyaluronate are mixed and need to be tumbled over night. The mixture is filled into containers with a suitable volume. These steps are performed in a sterile environment.

Unless otherwise defined, all technical and scientific terms used herein have the same meaning as commonly understood by one of ordinary skill in the art to which this invention belongs. Suitable methods and materials are described below, although methods and materials similar or equivalent to those described herein can also be used in the practice or testing of the present invention. All publications, patent applications, patents, and other references mentioned herein are incorporated by reference in their entirety. In case of conflict, the present specification, including definitions, will control. In addition, the materials, methods, and examples are illustrative only and not intended to be limiting.

Below, the invention is described in the appended examples, which are intended to illustrate the invention, without limiting the scope of protection.

EXAMPLES

Example 1

This example shows a process for autoclaving sodium hyaluronate dissolved in a buffer. The temperature for the autoclave chamber, the temperature in the containers containing the sodium hyaluronate and the $F_0$ value plotted against the time is shown in FIG. 4.

18 mg/ml sodium hyaluronate was dissolved in a buffer with the following content.

Buffer 0.05 M Arg, HCl
0.05 M Gly
0.05 M Lys, HCl
0.16 M NaCl
0.04 M $CaCl_2 2H_2O$ 600 ml of a solution was made and was tumbled until a homogeneous solution was obtained. This took about two days at room temperature. Two plastic bags were filled with 250 ml of the solution so that the thickness of the bags including the content was about 7 mm. The width, w, was 170 mm and the length, l, was 170 mm. The nominal volume of the bags was 1 l. Sensor A was placed in one of the bags and the autoclaving was started. Autoclaving was done with a fan autoclaving program using counter pressure and the cooling starts when $F_0>8$. The curves in the FIG. 4 show the temperature in the autoclave chamber, the temperature in the bag from sensor A and the calculated $F_0$ value plotted against the time in minutes. The curve for heating and cooling of the chamber is dependent of the autoclave. For safety reason, the autoclave is closed until the bag is cooled to 80° C. Otherwise the bag could have been removed when the temperature of the container was below 100° C.

It can be seen in the FIG. 4 that the temperature quickly reaches 121° C. in the bag, after about 4 minutes. Cooling is started when $F_0>8$. The temperature in the solution remains at above 121° C., for a few minutes. The temperature decreases on account of cooling of the chamber. When the temperature in the bag have reached about 80° C., the autoclave is opened and the bags are removed. The heating time is very short and the cooling time is also rather short. Conventional sterilization times may be around 30 minutes at around 121° C., excluding the cooling and heating time. The whole process in this Example was completed after 17 minutes.

Example 2

This Example shows the viscosity of hyaluronate autoclaved according to the invention and the viscosity of Healon® is shown as comparison.

Two runs of autoclaving of hyaluronate were done at different times. 18 mg/ml hyaluronate was dissolved in a solution comprising 0.05 M Arg, HCl
0.05 M Gly
0.05 M Lys, HCl
0.16 M NaCl
0.04 M $CaCl_2 2H_2O$.

The solution was tumbled for about two days to get a homogeneous solution. Then the solution was autoclaved in the same way as in Example 1. After the autoclaving, the solution was tumbled for another day and then viscosimetric measurement was done on the solution. Rotational viscosimetry was performed at different shear rates at 37° C. on a Stress Tech reometer on a volume of 0.6 ml.

Figure 5:
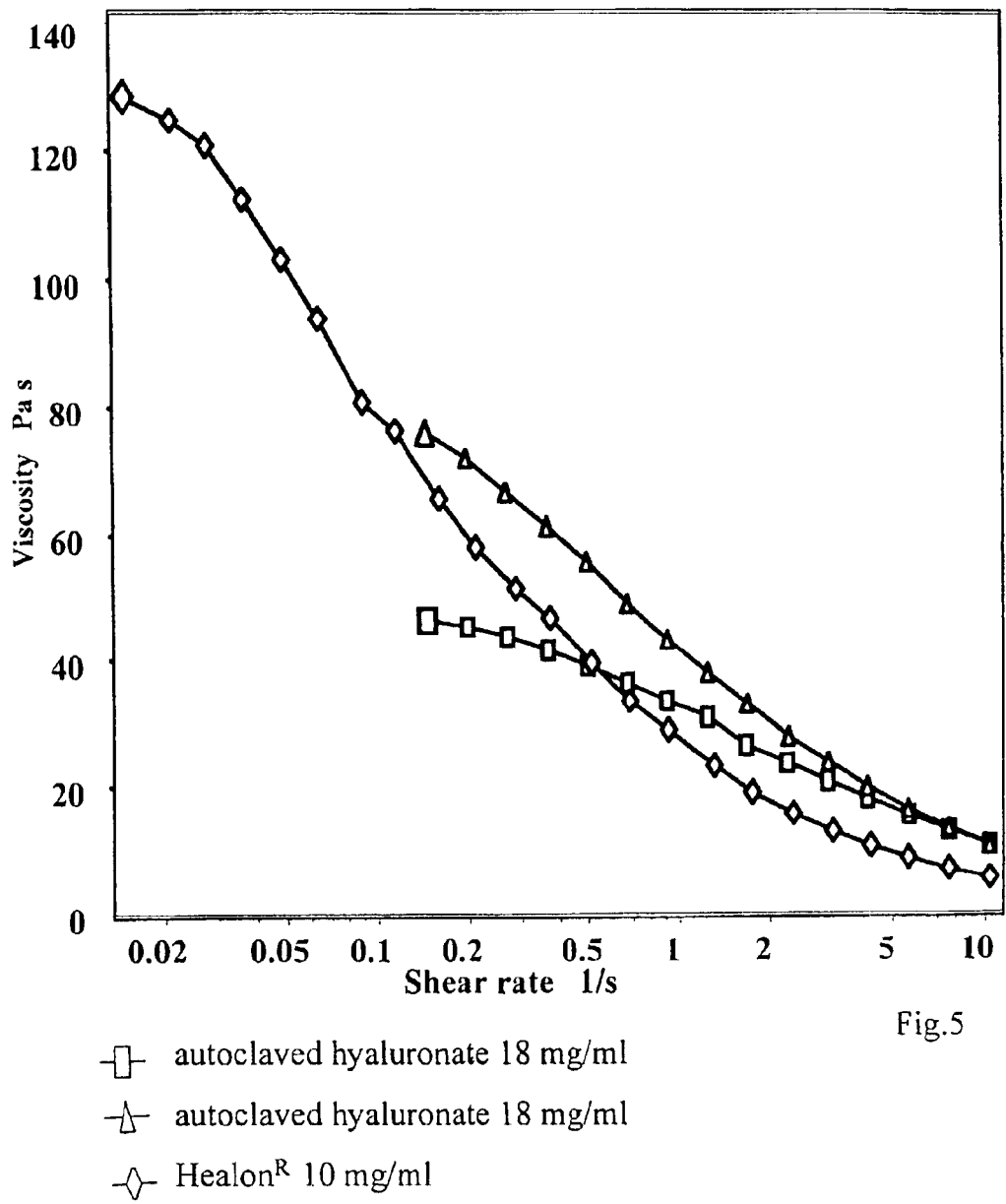
FIG. 5 is a graph depicting the viscosity curves of autoclaved sodium hyaluronate and Healon® against shear rate from Example 2.

The same viscosimetric measurement was done on Healon® from Pharmacia AB. The Healon® had a concentration of hyaluronic acid of 10 mg/ml. The result is shown in FIG. 5, where the viscosity is plotted against the shear rate.

Healon® has a viscosity, which is good for medical application. It can be shown in the FIG. 5 that the hyaluronate autoclaved according to the invention has a viscosity on the same level as Healon®, which is an acceptable level. Thus, the autoclaving according to the invention is mild to the viscosity and the molecular weight of hyaluronate.

It has been shown by the two Examples that bulk autoclaving is possible to do on hyaluronate and the viscosity and molecular weight is reduced to an acceptable level. This is new, since bulk autoclaving of hyaluronic acid has not been possible, due to the high degradation of the hyaluronic acid. With the new process according to the invention, it is now possible and the autoclaved hyaluronic acid has a wide area of application.

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A method for bulk autoclaving of polysaccharides, wherein the method comprises:

dissolving polysaccharides in an aqueous solution at a pH of about 6 to 8 and mixing until a homogeneous solution is obtained;

placing the resulting homogeneous solution in at least one container in an amount such that the at least one container comprises at least about 250 ml of the homogeneous solution and the thickness of the at least one container including the solution is less than 15 mm;

placing the at least one container containing the homogeneous solution in an autoclave;

placing a sensor in the at least one container; and autoclaving the at least one container containing the homogeneous solution, wherein the autoclaving comprises heating the homogeneous solution, and starting cooling when $F_0 > 8$.

2. The method of claim 1, wherein the $F_0$ value reaches maximally about 10 to 12 during the autoclaving method.

3. The method of claim 1, wherein the thickness of the container containing the homogeneous solution is less than 10 mm.

4. The method of claim 3, wherein the thickness of the container containing the homogeneous solution is less than 7 mm.

5. The method of claim 1, wherein the container is a plastic bag.

6. The method of claim 5, wherein a counter-pressure is used to avoid inflation of the bag.

7. The method of claim 6, wherein the counter-pressure is performed by means of nitrogen gas.

8. The method of claim 1, wherein the autoclaving comprises heating the homogeneous solution to a temperature in the range of 121 to 130° C.

9. The method of claim 8, wherein the homogeneous solution is heated to the temperature within about 3 to 7 minutes.

10. The method of claim 9, wherein the homogeneous solution remains at the temperature for 3 to 6 minutes.

11. The method of claim 10, wherein the homogeneous solution is cooled for about 5 to 12 minutes to a temperature of about 65 to 90° C.

12. The method of claim 11, wherein the autoclaving method is completed after about 11 to 25 minutes.

13. The method of claim 1, wherein the polysaccharides comprise glucose aminoglycans.

14. The method of claim 13, wherein the glucose aminoglycans comprise heparin sulfate, chondroitin sulfate, or their salts.

15. The method of claim 1, wherein the polysaccharides comprise carboxymethyl cellulose, xanthan, gum arabic, starch, or their salts.

16. The method of claim 1, wherein the polysaccharides comprise hyaluronic acid or salts.

17. The method of claim 16, wherein the hyaluronic acid is sodium hyaluronate.

18. The method of claim 17, wherein the sodium hyaluronate is dissolved in a buffer comprising 0.045 to 0.055 M Arg, HCl
0.045 to 0.055 M Gly
0.045 to 0.055 M Lys, HCl
0.01 to 0.18 M NaCl
0.035 to 0.045 M $CaCl_2 2H_2O$ and the hyaluronate is dissolved in an amount of at most 23 mg/ml.

19. The method of claim 18, wherein the hyaluronate is dissolved in an amount of 10–23 mg/ml.

20. The method of claim 1, wherein the method comprises placing at least one liter of the homogeneous solution in the at least one container prior to autoclaving.

* * * * *